(12) United States Patent
Rutel et al.

(10) Patent No.: US 12,419,602 B2
(45) Date of Patent: Sep. 23, 2025

(54) DEAD DETECTOR ELEMENT DETECTION

(71) Applicant: The Board of Regents of the University of Oklahoma, Norman, OK (US)

(72) Inventors: Isaac B Rutel, Choctaw, OK (US); Jonthomas Box, Oklahoma City, OK (US); Adam Salazar, Atlanta, GA (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 528 days.

(21) Appl. No.: 17/930,294

(22) Filed: Sep. 7, 2022

(65) Prior Publication Data
US 2023/0079742 A1     Mar. 16, 2023

Related U.S. Application Data

(60) Provisional application No. 63/241,376, filed on Sep. 7, 2021.

(51) Int. Cl.
   *A61B 6/58*        (2024.01)
   *G06V 10/774*      (2022.01)
   *G06V 10/776*      (2022.01)
   *G06V 20/70*       (2022.01)

(52) U.S. Cl.
   CPC .......... *A61B 6/586* (2013.01); *G06V 10/774* (2022.01); *G06V 10/776* (2022.01); *G06V 20/70* (2022.01)

(58) Field of Classification Search
   CPC ...... A61B 6/586; G06V 20/70; G06V 10/774; G06V 10/776
   See application file for complete search history.

(56) References Cited

U.S. PATENT DOCUMENTS

| 11,521,301 | B2* | 12/2022 | Klaiman | .................. G06N 3/04 |
| 12,051,482 | B2* | 7/2024 | Linnen | .................... G11C 11/54 |
| 2015/0029368 | A1 | 1/2015 | Pyeoun et al. | |
| 2016/0342843 | A1 | 11/2016 | Yuan et al. | |

(Continued)

OTHER PUBLICATIONS

Zhang, "Bridge Damage Detection using a Single-Stage Detector and Field Inspection Images", Feb. 23, 2019, HCUST Publication, pp. 1-12 (Year: 2019).*

(Continued)

*Primary Examiner* — Elias Desta
(74) *Attorney, Agent, or Firm* — Conley Rose, P.C.

(57) ABSTRACT

A method comprises: performing training and testing of an initial machine model to create a final machine model, wherein the training and testing use focal loss; performing detection of dead detector elements in a digital detector of a second digital radiographic (DR) imaging system using the final machine model; and determining whether to replace or keep the digital detector based on the detection. An apparatus comprises: a memory; and a processor coupled to the memory and configured to: perform training and testing of an initial machine model to create a final machine model, wherein the training and testing use focal loss; perform detection of dead detector elements in a digital detector of a second digital radiographic (DR) imaging system using the final machine model; and determine whether to replace or keep the digital detector based on the detection.

21 Claims, 13 Drawing Sheets

(56) References Cited

U.S. PATENT DOCUMENTS

| | | |
|---|---|---|
| 2016/0350936 A1 | 12/2016 | Korchev et al. |
| 2017/0039727 A1 | 2/2017 | Korchev et al. |
| 2017/0074995 A1 | 3/2017 | Laurence et al. |
| 2017/0180659 A1 | 6/2017 | Levoy et al. |
| 2017/0237919 A1 | 8/2017 | Lamesch |
| 2018/0012542 A1 | 1/2018 | Lee et al. |
| 2018/0150942 A1 | 5/2018 | Zeng |
| 2019/0361136 A1 | 11/2019 | Song et al. |

OTHER PUBLICATIONS

Aufrichtig, Richard, et al.; "Measurement of the Noise Power Spectrum in Digital X-Ray Detectors"; Proceedings of SPIE 4320, Medical Imaging 2001: Physics of Medical Imaging; Jun. 28, 2001; 12 pages.

Cui, Sunan, et al.; "Introduction to Machine and Deep Learning for Medical Physicists"; Med. Phys.; vol. 47, No. 5; May 15, 2020; 21 pages.

Geiser, William R., et al.; "Challenges in Mammography: Part 1, Artifacts in Digital Mammography"; AJR:197; Dec. 2011; 8 pages.

Grandini, Margherita, et al.; "Metrics for Multi-Class Classification: An Overview"; arXiv:2008.05756v1; Aug. 13, 2020; 17 pages.

Lin, Tsung-Yi, et al.; "Focal Loss for Dense Object Detection"; arXiv:1708.02002v2; Feb. 7, 2018; 10 pages.

May, R.J., et al.; "Data Splitting for Artificial Neural Networks using SOM-Based Stratified Sampling"; Neural Networks; vol. 23; 2010; 12 pages.

Padgett, R., et al.; "Assessment of the Effects of Pixel Loss on Image Quality in Direct Digital Radiography"; Institute of Physics Publishing; Physics in Medicine and Biology; vol. 49; Feb. 24, 2004; 10 pages.

Salazar, Adam Joseph; "The Role of Convolutional Networks in Identifying Dead Detector Elements within a Diagnostic Imaging System"; The University of Oklahoma Health Sciences Center Graduate College; May 8, 2020; 101 pages.

Tan, Man, et al.; "Pulmonary Nodule Detection Using Hybrid Two-Stage 3D CNNs"; Med. Phys.; vol. 47, No. 8; Jul. 6, 2020; 13 pages.

Wang, Yapin, et al.; "Human Peripheral Blood Leukocyte Classification Method based on Convolutional Neural Network and Data Augmentation"; Med. Phys.; vol. 47, No. 1; Nov. 22, 2019; 10 pages.

Wu, Yue, et al.; "Local Shannon Entropy Measure with Statistical Tests for Image Randomness"; Information Sciences; vol. 222; Aug. 7, 2012; 20 pages.

Ying, Xue; "An Overview of Overfitting and its Solutions"; J. Phys.: Conf. Ser. 1168; 2019; 7 pages.

* cited by examiner

DEAD DETECTOR ELEMENT DETECTION

CROSS-REFERENCE TO RELATED APPLICATIONS

This claims priority to U.S. Prov. Patent App. No. 63/241,376 filed on Sep. 7, 2021, which is incorporated by reference.

STATEMENT REGARDING FEDERALLY SPONSORED RESEARCH OR DEVELOPMENT

Not applicable.

BACKGROUND

Radiology is a medical discipline that implements medical imaging to diagnose and treat diseases of humans and animals. Medical imaging techniques include x-ray, ultrasound, CT, PET, fluoroscopy, and MRI. Diagnostic radiology involves interpreting images to screen, diagnose, understand the causes of, and monitor diseases. Interventional radiology involves using imaging techniques to guide procedures such as device insertion, angioplasty, embolization, ablation, and biopsy. Medical imaging is a sensitive technology, so accurate results depend on accurate imaging systems.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
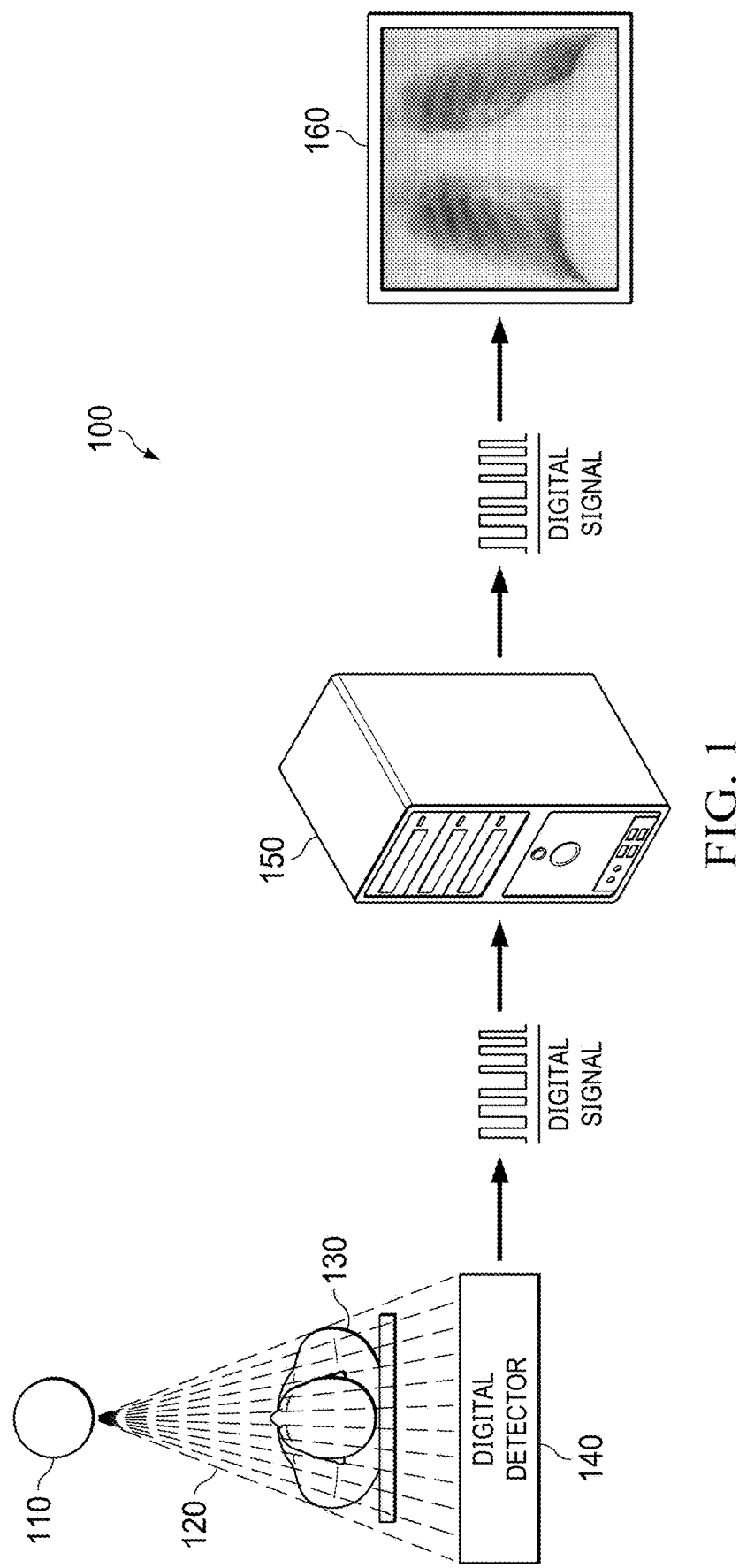
FIG. 1 is a schematic diagram of an imaging environment.

It should be understood at the outset that, although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The following abbreviations apply:
ADC: analog-to-digital converter
AI: artificial intelligence
ASIC: application-specific integrated circuit
CNN: convolutional neural network
CPU: central processing unit
CT: computed tomography
DAC: digital-to-analog converter
DR: digital radiographic
DSP: digital signal processor
EO: electrical-to-optical
FFT: fast Fourier transform
FN: false negative
FP: false positive
FPGA: field-programmable gate array
kVp: kilovoltage peak
mAs: milliampere-second(s)
mm: millimeter(s)
MRI: magnetic resonance imaging
ms: millisecond(s)
NPS: noise power spectrum
OBI: on-board imaging
OE: optical-to-electrical
PET: positron emission tomography
RAM: random-access memory
RF: radio frequency
RGB: red, green, and blue
ROM: read-only memory
RX: receiver unit
SRAM: static RAM
TCAM: ternary content-addressable memory
TP: true positive
TX: transmitter unit
2D: two-dimensional.

Before further describing various embodiments of the apparatus, component parts, and methods of the present disclosure in more detail by way of exemplary description, examples, and results, it is to be understood that the embodiments of the present disclosure are not limited in application to the details of apparatus, component parts, and methods as set forth in the following description. The embodiments of the apparatus, component parts, and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the apparatus, component parts, and methods of the present disclosure have been described in terms of particular embodiments, it will be apparent to those of skill in the art that variations may be applied to the apparatus, component parts, and/or methods and in the steps or in the sequence of steps of the method described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms and phrases, unless otherwise indicated, shall be understood to have the following meanings: The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The phrase "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the apparatus, composition, or the methods or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The terms "about" or "approximately", where used herein when referring to a measurable value such as an amount, percentage, temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units therefore refers to and includes all values or ranges of values of the units, and fractions of the values of the units and integers within said range, including for example, but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of about 100 units to about 2000 units therefore can be used to set the lower and upper boundaries of a range in accordance with the embodiments of the present disclosure. More particularly, a range of 10-12 units includes, for example, 10, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, and 12.0, and all values or ranges of values of the units, and fractions of the values of the units and integers within said range, and ranges which combine the values of the boundaries of different ranges within the series, e.g., 10.1 to 11.5.

FIG. 1 is a schematic diagram of an imaging environment 100. The imaging environment 100 comprises a radiation element 110, radiation 120, a patient 130, a digital detector 140, an ADC 150, a computer 160, a DAC 170, and a screen 180. The radiation element 110, the digital detector 140, the ADC 150, the computer 160, the DAC 170, and the screen 180 form a DR imaging system.

In operation, the radiation element 110 emits the radiation 120 towards the patient 130. As the radiation 120 passes through the patient 130, the radiation 120 absorbs in different parts of the patient 130 at different rates, resulting in unabsorbed radiation 120 that passes through the patient 130. The digital detector 140 comprises thousands of detector elements that convert the unabsorbed radiation 120 incident on their surfaces into a digital signal. The computer 150 processes and stores the digital signal. The screen 180 displays the digital signal as an image. A radiologist reviews the image for diagnostic or interventional purposes.

The integrity of the DR imaging system directly depends on the integrity of the detector elements. Dead detector elements are those that fail to convert the unabsorbed radiation 120 into the analog signal. The DR imaging system may be manufactured with a certain number of dead detector elements, or detector elements may die over time due to normal wear and tear or due to damage from the radiation 120. Vendor-specific software locates and corrects for the dead detector elements so that the image properly displays on the screen 180 with no pixel errors that would indicate dead detector elements. But even when corrected for, dead detector elements constitute a degradation of the quality of the image.

There exists a theoretical limit on the number of allowable dead detector elements in a system beyond which the DR imaging system must be replaced because the level of image degradation is too high for clinical use. This limit, the actual number of dead detector elements in the digital detector 140, and the algorithms used to correct for them are, as a general rule, solely the knowledge of the vendor. This makes the clinician, for instance the medical physicist who is responsible for the quality of the detection system, dependent upon a third party whose goals may or may not align with that of the patient 130. There is therefore a desire for the clinician to determine the number of dead detector elements, as well as the limit and algorithms described above.

Disclosed herein are embodiments for dead detector element detection. The embodiments train, test, and validate a CNN capable of localizing and estimating dead detector elements in a DR imaging system given a set of images taken on that system. The CNN comprises convolutional layers, fully-connected layers, and a dropout layer. The CNN is trained and tested using processed images. The processed images result from performing calculations on images. The calculations represent spatially-oriented relationships. For instance, the calculations comprise NPS and entropy calculations. The CNN is trained and tested using focal loss. The training and testing result in a final machine model. A clinician may perform detection of dead detector elements using the final machine model. Based on that detection, the clinician can decide whether to replace the digital detector. Thus, the embodiments limit the clinician's reliance on vendors.

Figure 2:
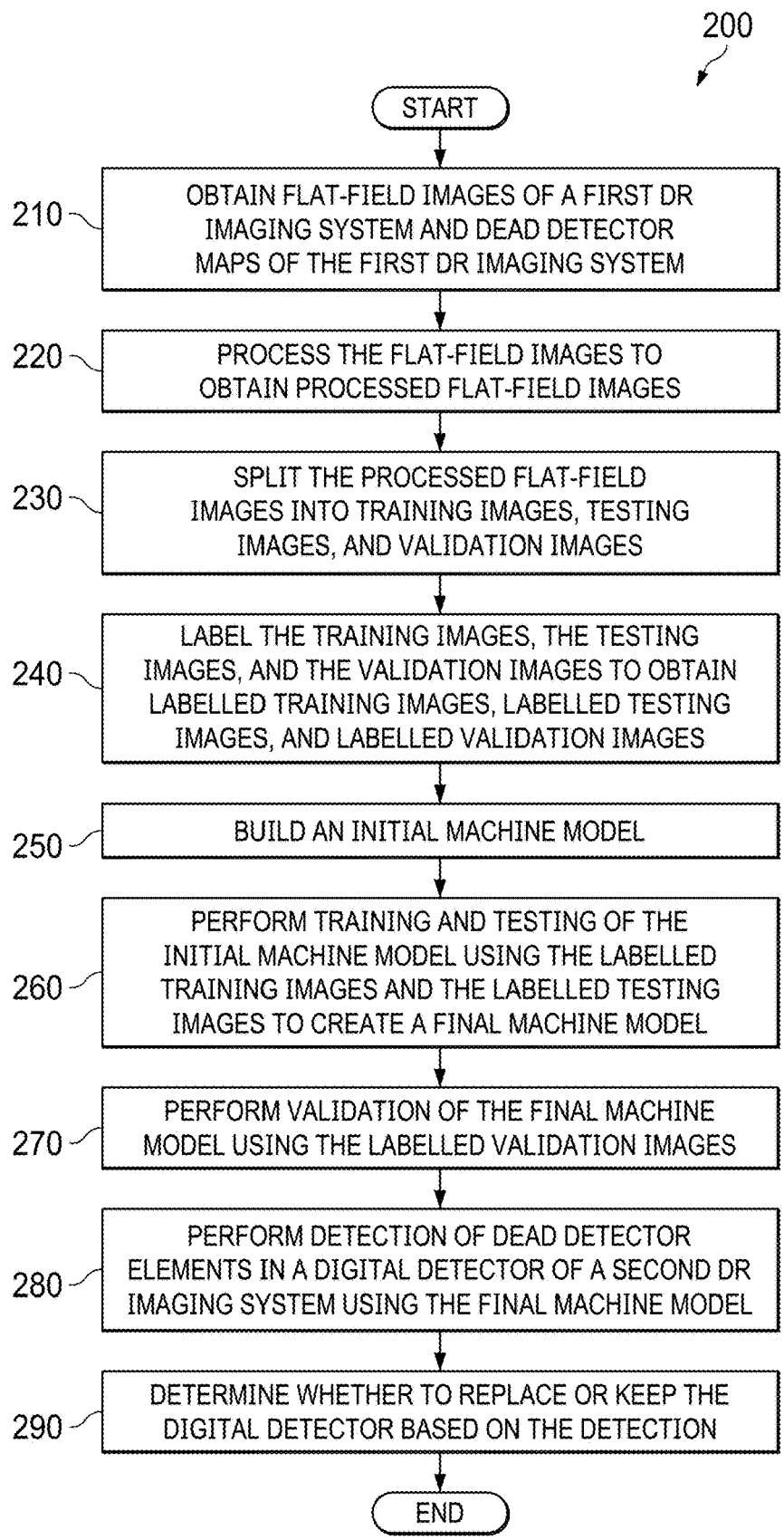
FIG. 2 is a flowchart illustrating a method of dead detector element detection.

FIG. 2 is a flowchart illustrating a method 200 of dead detector element detection. At step 210, flat-field images of a first DR imaging system and dead detector maps of the first DR imaging system are obtained. Flat-field images are images obtained without an object, for instance the patient 130, in the path of the radiation 120. Flat-field images are composed of noise characteristics of the digital detector 140 and vendor-corrected pixel data. The dead detector maps, or dead pixel maps, display the location of dead detector elements. The dead detector maps provide the ground truth for training, testing, and validation of a CNN.

Figure 3:
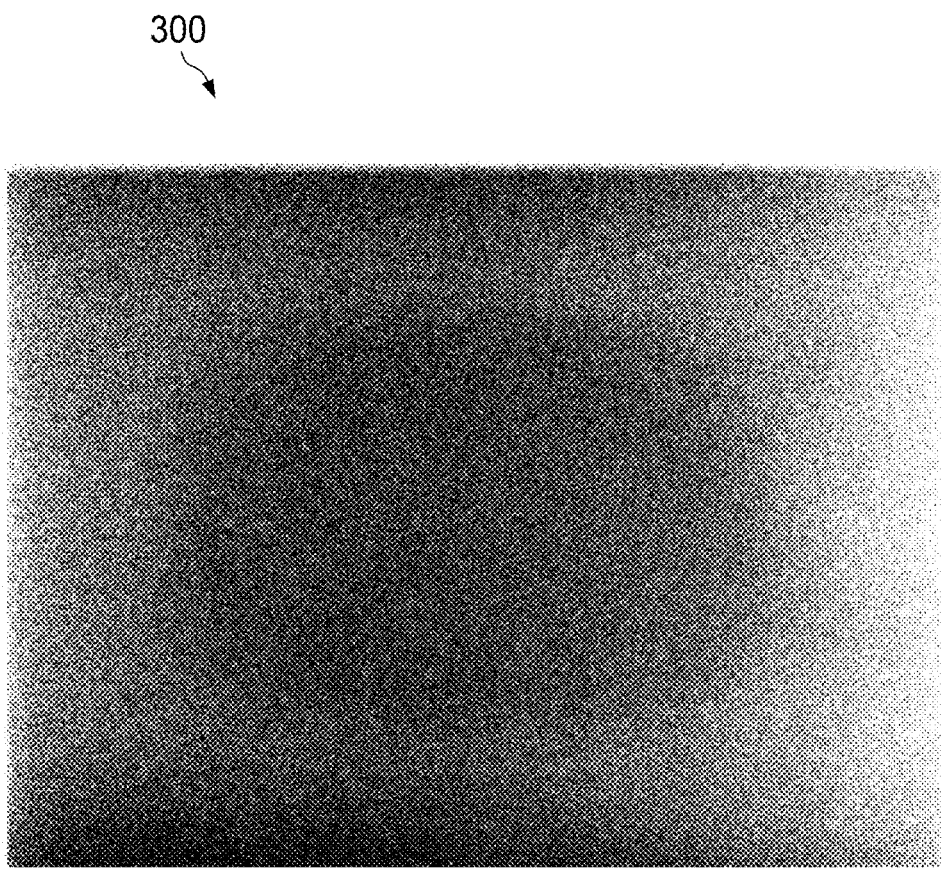
FIG. 3 is a flat-field image.

FIG. 3 is a flat-field image 300. The flat-field image 300 may be one of the flat-field images in step 210. Pixels in the flat-field image 300 show the number of x-rays that have interacted with corresponding detector elements of the digital detector 140. This may generally produce an image which shows random x-ray radiation information about a mean value with little to no structure. In the flat-field image 300, there is some residual structure in the form of a central oval, which indicates the digital detector 140 may not fully compensate for gain differences in individual detector electronics or a prior gain calibration which included some residual dose on a plate of the digital detector 140. The central oval suggests the profile of an x-ray image, where the central rays provide more interactions, while outer detectors receive fewer x-rays.

In an experiment, the flat-field images comprised 61 flat-field images taken using OBI systems of radiotherapy linear accelerators. The flat-field images were taken with a range of kVp, mA, ms, and copper filtration thickness values shown in Table 1 to model various image acquisition conditions.

TABLE 1

| Flat-field image values | |
| --- | --- |
| kVp | 60, 75, 80, 100, 120 |
| mA | 10, 200, 250 |
| ms | 50; 250; 2,500 |
| copper filtration thickness (mm) | 0, 1, 2 |

The dead detector maps were acquired from vendors of both linear accelerators.

Returning to FIG. 2, at step 220, the flat-field images are processed to obtain processed flat-field images. The processing includes dividing the images into sub-images, performing calculations on each sub-image, and adding the calculations to the sub-images. The calculations may represent any spatially-oriented relationships. For instance, the calculations comprise NPS calculations or entropy calculations, which are stacked with pixel values as pseudo color channels. Pseudo color channels contrast to actual color channels, which represent components of color, for instance, red, green, and blue in an RGB scheme.

Because the flat-field images are noisy, the pseudo color channel approach helps find anomalies that do not look like noise. Specifically, such anomalies are areas that appear not to be random, but instead appear to be correlated. The anomalies may therefore indicate vendor corrections.

The NPS calculation is a 2D FFT. It is used because uncorrelated noise should provide a relatively constant NPS, while correlated noise tends to show slope variations in the spectrum when noise power is plotted against the spatial resolution. If there are sub-images with correlated noise, then there should be patterns in the NPS that would relate to an a priori calculation between image pixels. The CNN can use the calculation as a contrast to determine that the sub-image is associated with dead detector elements that have been corrected.

The entropy calculation characterizes any information loss produced via pixel correction algorithms. The entropy calculation involves calculating the Shannon entropy of each sub-image according to equation (1):

$$H(X) = -\Sigma_{i=1}^{L-1} P_i \log P_i. \quad (1)$$

H is the Shannon entropy of sub-image X, L is the bit depth of the sub-image, and $P_i$ is the probability of a pixel in the sub-image having pixel value i. The entropy calculation is used because any correction algorithm that replaces a dead detector element's pixel value with a mean pixel value of local pixels would reduce the number of pixels in the sub-image and thus reduce $P_i$ and the entropy of the sub-image.

Figure 4:
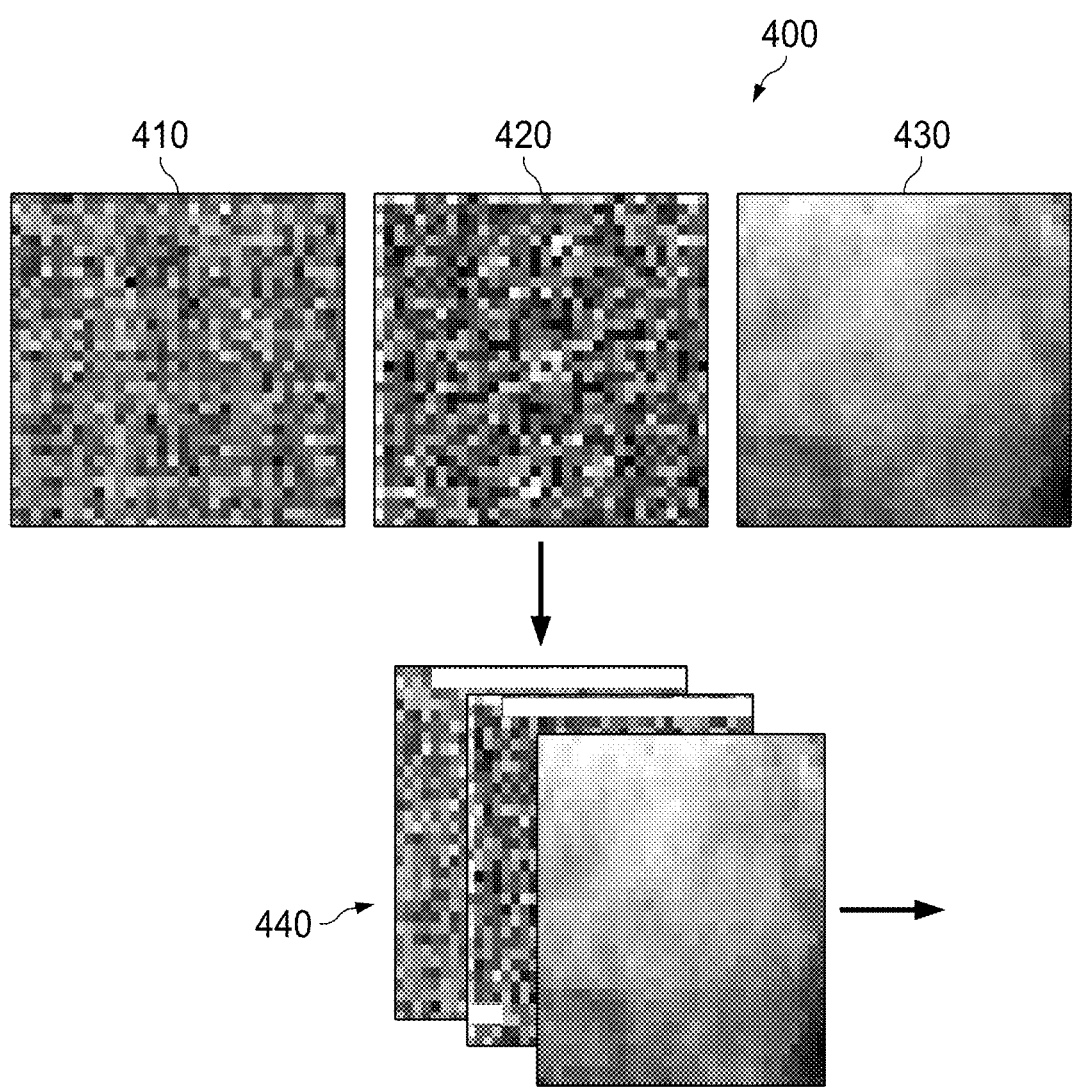
FIG. 4 is a diagram demonstrating stacking pseudo color channels.

FIG. 4 is a diagram 400 demonstrating stacking pseudo color channels. As shown, a pixel-value pseudo color channel 410, an NPS pseudo color channel 420, and an entropy pseudo color channel 430 are stacked together to form a stacked sub-image 440. Though the pixel-value pseudo color channel 410, the NPS pseudo color channel 420, and the entropy pseudo color channel 430 are shown, other pseudo color channels which quantify spatial dependence are possible. Spatial dependence is any non-zero result from calculating the spatial autocorrelation of an image. This may be satisfied when pixel values are related through mathematical computation to other pixel values in the image, for example, if a central pixel is the result of an averaging over several pixels which surround the central pixel.

In the experiment, the flat-field images comprised 1,536× 2,048 grayscale pixels, or 65,536 total pixels, with a bit depth of $2^{16}$. Each image was split into 32×32 sub-images to localize dead detector elements using a classification scheme. As a result of the NPS calculation and the entropy calculation, each sub-image increased its dimension from 32×32×1 to 32×32×3.

Returning to FIG. 2, at step 230, the processed flat-field images are split into training images, testing images, and validation images. First, a specified number of the validation images are randomly removed from the processed flat-filed images. Second, the remaining processed flat-field images are randomly split and stratified into the training images and the testing images in order to ensure proportional class representation in the training images and the testing images.

In the experiment, the specified number is 5. The splitting was performed using the Scikit-learn library's train_test_split function.

At step 240, the training images, the testing images, and the validation images are labelled to obtain labelled training images, labelled testing images, and labelled validation images, respectively. The training images, the testing images, and the validation images are labelled based on a percent of dead detector element pixels among the 65,536 total pixels. Dead detector element pixels are pixels that correspond to dead detector elements based on the dead detector maps.

In the experiment, a label of class 0 indicates no dead detector element pixels, a label of class 1 indicates 0-1% dead detector element pixels, a label of class 2 indicates 1-5% dead detector element pixels, and a label of class 3 indicates greater than 5% dead detector element pixels.

Figure 5:
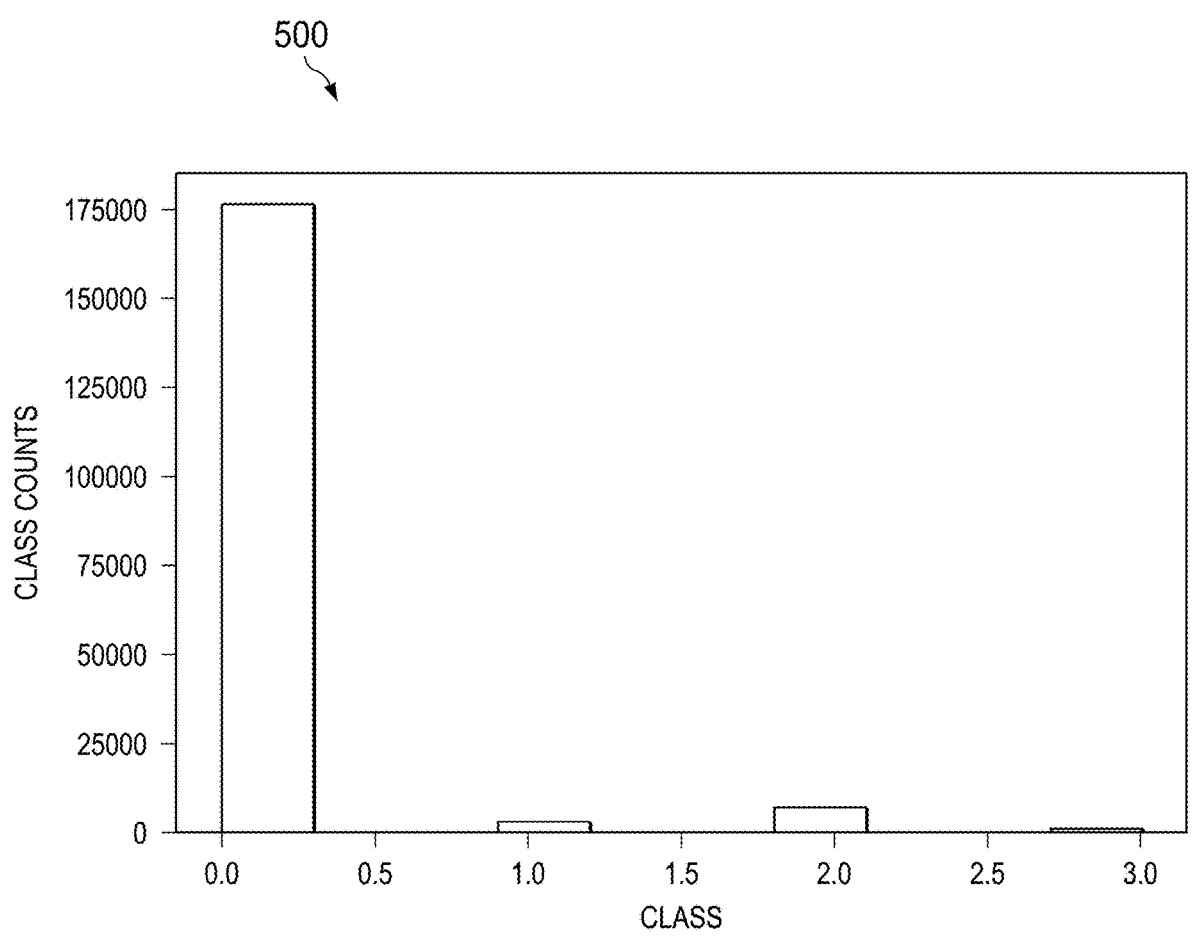
FIG. 5 is a histogram demonstrating labelling in the experiment.

FIG. 5 is a histogram 500 demonstrating labelling in the experiment. The x-axis represents classes. The classes are class 0, 1, 2, and 3. The y-axis represents class counts. As shown, among the labelled testing images and the labelled training images, the class distribution was imbalanced so that over 90% of the labelled testing images and the labelled training images had no dead detector element pixels.

Returning to FIG. 2, at step 250, an initial machine model is built.

Figure 6:
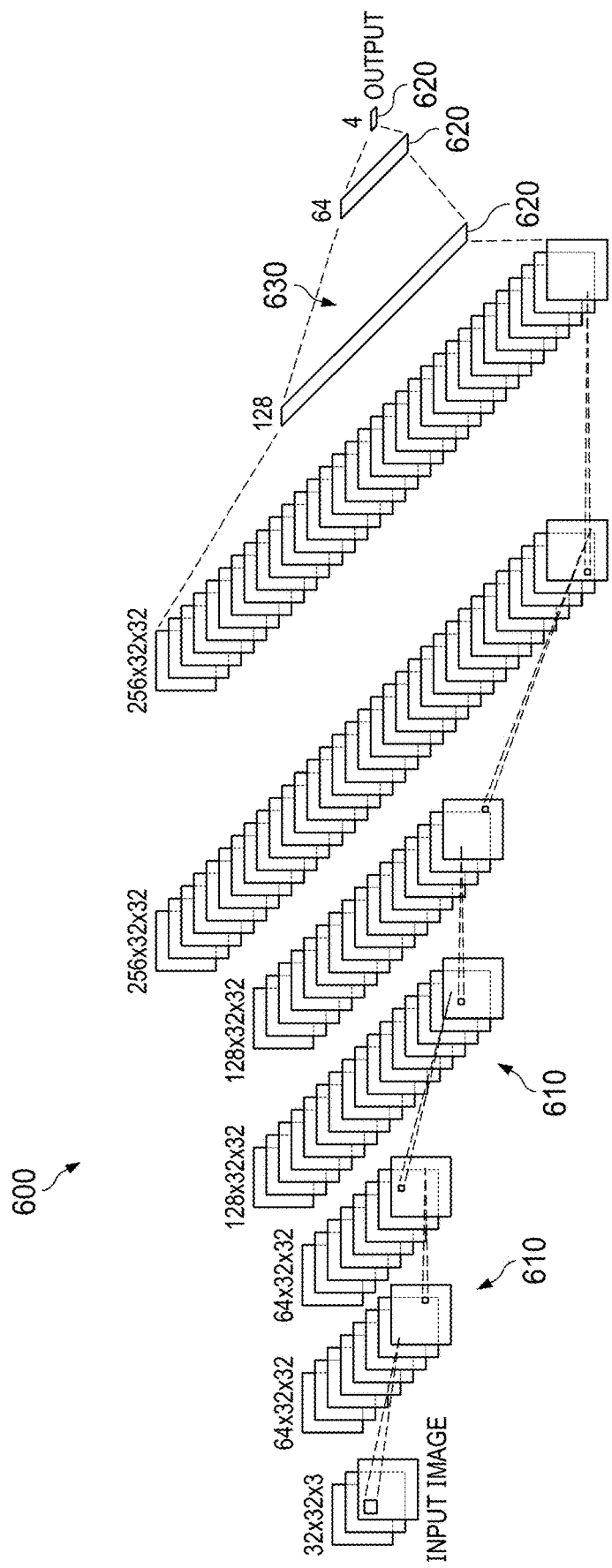
FIG. 6 is a schematic diagram of a CNN.

FIG. 6 is a schematic diagram of a CNN 600. The CNN 600 may implement the initial machine model in step 250 of FIG. 2. The CNN 600 comprises 6 convolutional layers 610, 3 fully-connected layers 620, and a 30% dropout layer 630. Though 6 convolutional layers 610, 3 fully-connected layers 620, and 1 30% dropout layer 630 are shown, the CNN 600 may comprise different numbers of each layer, and those numbers may be optimized.

The convolution layers 610 perform a convolution operation for each previous iteration-generated kernel, creating feature maps from which the CNN 600 may learn. The fully-connected layers 620 are fully connected to all activations in the previous layer, further forming the CNN 600 into a standard feed-forward configuration. The dropout layer 630 removes neurons from the first fully-connected layer 620 as a mechanism to help improve convergence and prevent overfitting.

Returning to step 250 in FIG. 2, in building the initial machine model, batch normalization is performed between all convolutional layers 610 and fully connected layers 620. In the experiment, the initial machine model was built using Python 3.7 and TensorFlow 2.3.0.

At step 260, training and testing are performed on the initial machine model using the labelled training images and the labelled testing images, respectively, to create a final machine model. Each iteration between the initial machine model and the final machine model is trained and tested to evaluate for overfitting and underfitting. Overfitting occurs when the machine model does not generalize well to new data because it has learned the training set, in this case the labelled training images, too well. Underfitting occurs when the machine model does not learn the training set well enough and therefore exhibits poor performance. Between each round of training, model hyper-parameters are adjusted to create a new machine model. The new machine model is evaluated using focal loss or cross-entropy loss of the test set, in this case the labelled testing images. If a machine model's testing performance is significantly worse than the machine model's training performance, then the machine model is overfit. If a machine model's focal loss for both training and testing is worse than previous machine models' focal loss, then the machine model is underfit.

Using focal loss to evaluate new machine models addresses the imbalance in class distribution among the labelled testing images and the labelled training images described above and therefore improves model performance. Focal loss is an extension of cross-entropy loss, which is a loss function used in classification-type problems. The focal loss adds a factor of $\alpha_t (1-p_t)^\gamma$ to the formula for cross-entropy loss, resulting in the following loss function:

$$FL = -\alpha_t (1-p_t)^\gamma \log(p_t). \tag{2}$$

FL is the focal loss. $\alpha_t$ is a tunable balancing parameter that is a weighting factor and takes into account class representation in the data. p is the probability of the estimated class so that $p_t = p$ for the most represented class and $p_t = 1-p$ for all other classes. $\gamma$ is a tunable focusing parameter that adjusts a loss contribution from easily-classified examples, which results in an increased importance of correcting misclassified examples. Multiplying the cross-entropy loss formula by $\alpha_t (1-p_t)^\gamma$ provides a loss function that focuses on learning the most difficult and least represented classes in a classification problem.

After iterating until a machine model fits the labelled training images and the labelled testing images, the final machine model is evaluated using a confusion matrix, a precision, a recall, and an $F_1$ score as follows:

$$\text{Precision} = \frac{TP}{FP + TP} \tag{3}$$

$$\text{Recall} = \frac{TP}{FN + TP} \quad (4)$$

$$F_1 = 2 * \frac{\text{Precision} * \text{Recall}}{\text{Precision} + \text{Recall}} = \frac{TP}{\frac{(FN = FP)}{2} + TP}. \quad (5)$$

TP, FP, and FN have standard definitions of a total number of true positives, a total number of false positives, and a total number of false negatives, but are extended for use in a multi-class classification problem. In the multi-class classification problem, a single positive class is fixed and the other classes are negative classes. Precision and recall are calculated for the positive class, a new positive class is fixed, and the procedure is iterated until precision and recall are calculated for all classes. TP, FP, and FN are determined by comparing the result of the machine model to the corresponding dead detector map. $F_1$ is a harmonic mean that provides a measure of overall performance to be both selective and sensitive.

In the experiment, the hyper-parameters that were adjusted included the number of layers and the types of layers, $\alpha_t$ and $\gamma$ for focal loss, the type of optimizer used, and the number of epochs trained. Overfitting was further addressed through the use of an early stopping technique, which evaluated the test set loss after each epoch and terminated training if the test set loss did not decrease over a period of 50 epochs. Multiple values of $\alpha_t$ and $\gamma$ were evaluated during training and testing. It was determined that $\alpha_t$=0.25 and $\gamma$=4 provided the best combination. That combination was used in the final iteration of the machine model.

Figure 7:
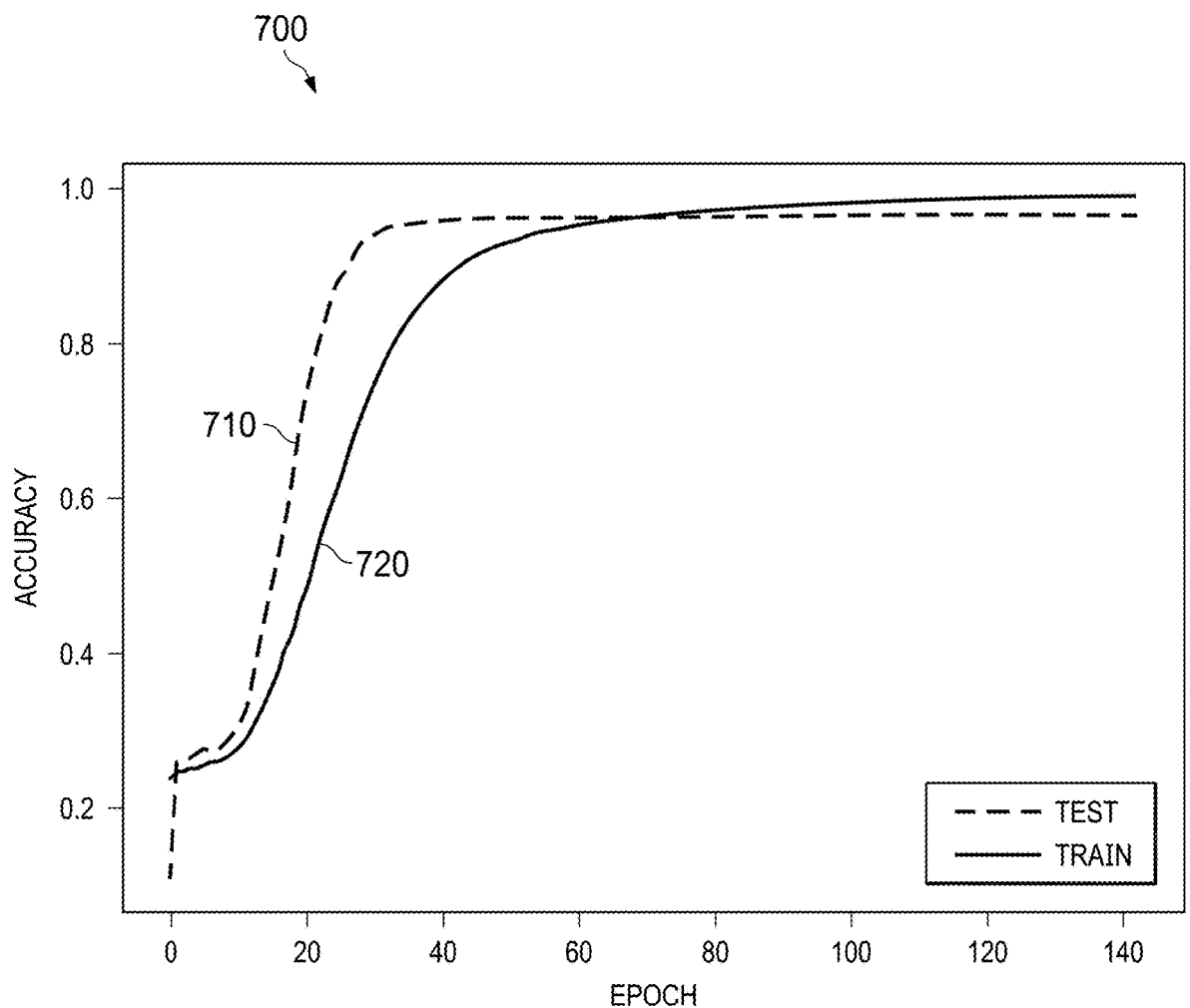
FIG. 7 is a graph demonstrating machine model accuracy obtained in the experiment.

FIG. 7 is a graph 700 demonstrating machine model accuracy obtained in the experiment. The x-axis represents epochs trained. The y-axis represents accuracy normalized to 1.0. The graph 700 shows a testing curve 710 representing accuracy of the testing and a training curve 720 representing accuracy of the training. The testing curve 710 and the training curve 720 demonstrate that CNN 600 improved until a plateau was reached between 30 and 60 epochs for the training and the testing, respectively. The testing curve 710 and the training curve 720 also demonstrate the importance of an early stopping technique in because, as the number of epochs increases beyond a certain point, the training will tend to outperform the testing, resulting in overfitting and poor model generalization.

Returning to FIG. 2, at step 270, validation is performed on the final machine model using the labelled validation images. The results of validation in the experiment are shown in Table 2.

TABLE 2

Final machine model performance using
the labelled validation images

| Model | Class | Precision | Recall | $F_1$ Score |
|---|---|---|---|---|
| Focal loss with contrast channels | 0 | 0.95 | 1.00 | 0.98 |
| | 1 | 1.00 | 0.12 | 0.21 |
| | 2 | 0.95 | 0.11 | 0.20 |
| | 3 | 1.00 | 0.50 | 0.67 |
| Focal loss with no contrast channels | 0 | 0.95 | 1.00 | 0.98 |
| | 1 | 0.93 | 0.12 | 0.21 |
| | 2 | 0.94 | 0.11 | 0.20 |
| | 3 | 1.00 | 0.50 | 0.67 |
| Cross-entropy loss with contrast channels | 0 | 0.95 | 1.00 | 0.98 |
| | 1 | 1.00 | 0.12 | 0.21 |
| | 2 | 0.95 | 0.11 | 0.20 |
| | 3 | 1.00 | 0.50 | 0.67 |

TABLE 2-continued

Final machine model performance using
the labelled validation images

| Model | Class | Precision | Recall | $F_1$ Score |
|---|---|---|---|---|
| Cross-entropy loss with no contrast channels | 0 | 0.95 | 1.00 | 0.98 |
| | 1 | 1.00 | 0.11 | 0.21 |
| | 2 | 0.84 | 0.14 | 0.25 |
| | 3 | 1.00 | 0.50 | 0.67 |

Table 2 shows that the CNN 600 can detect dead detector elements with nearly perfect precision, specifically, 0.84 or higher for all 4 classes. That means that 84% of positives are TPs. Use of focal loss, the NPS pseudo color channel 420, and the entropy pseudo color channel 430 decrease the number of FPs and FNs.

Performance was best for the majority class 0 corresponding to labelled validation images with no dead detector element pixels. All class 0 models have a high precision, recall, and $F_1$ score. Performance was second-best for class 3 corresponding to greater than 5% dead detector element pixels. All class 3 models had an $F_1$ score of 0.67. Performance was worst for class 1 corresponding to 0-1% dead detector element pixels and class 2 corresponding to 1-5% dead detector element pixels. The class 1 models and class 2 models had an average $F_1$ score of 0.21. However, because $F_1$ was similar for all models, a clinician could select a model based on what is most interesting to him or her. For instance, the user could select a model with the highest precisions for classes with fewer dead detector element pixels (e.g., class 0 and class 1) or a model with the highest recall for class 2.

Figure 8:
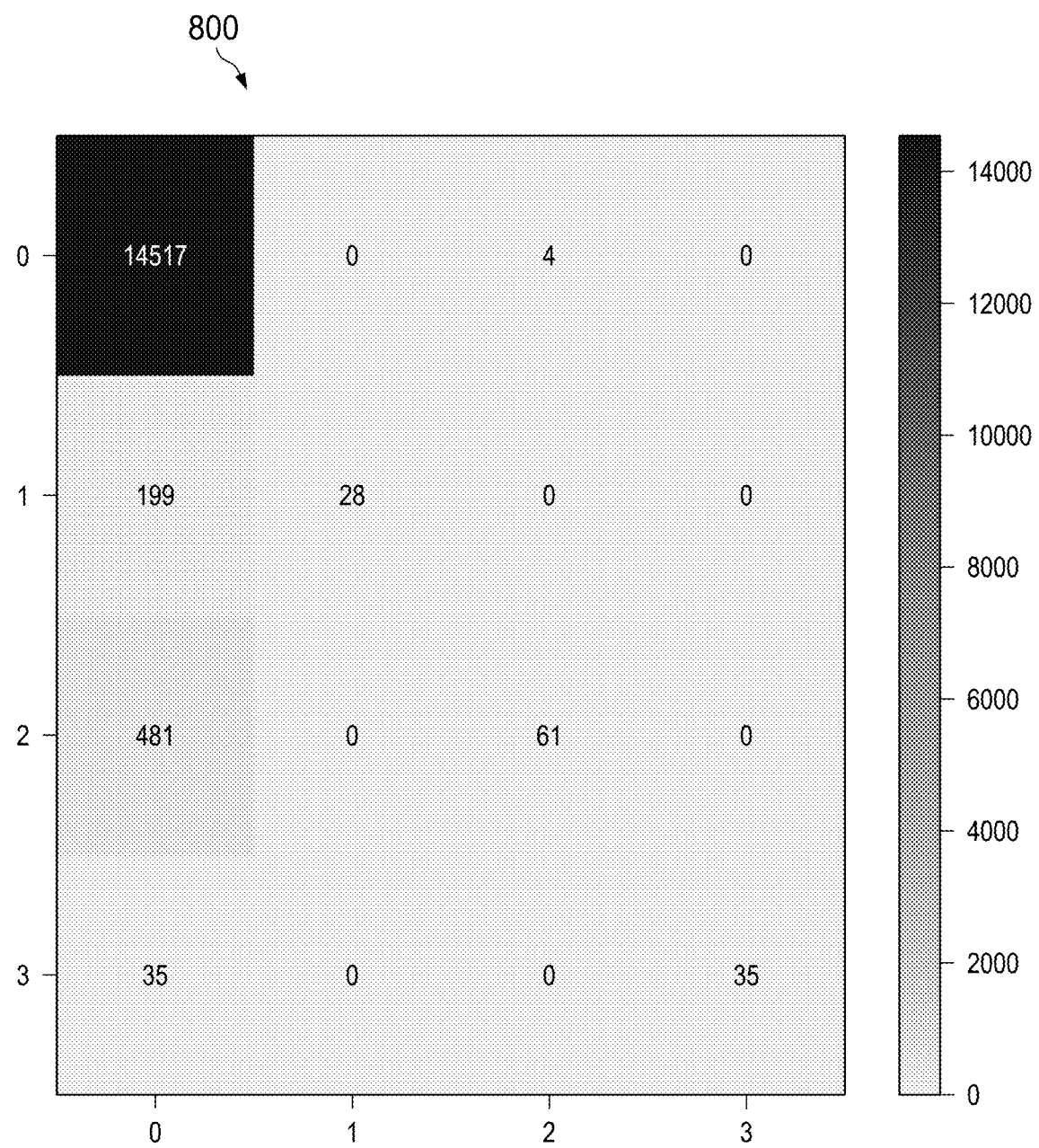
FIG. 8 is a confusion matrix of ground truth versus model prediction for a first model in the experiment.

FIG. 8 is a confusion matrix 800 of ground truth versus model prediction for a first model in the experiment. The x-axis represents model prediction. The y-axis represents ground truth. In the first model, focal loss, the NPS pseudo color channel 420, and the entropy pseudo color channel 430 were used. Diagonal elements of the confusion matrix 800 correspond to correctly-classified labelled validation images.

Figure 9:
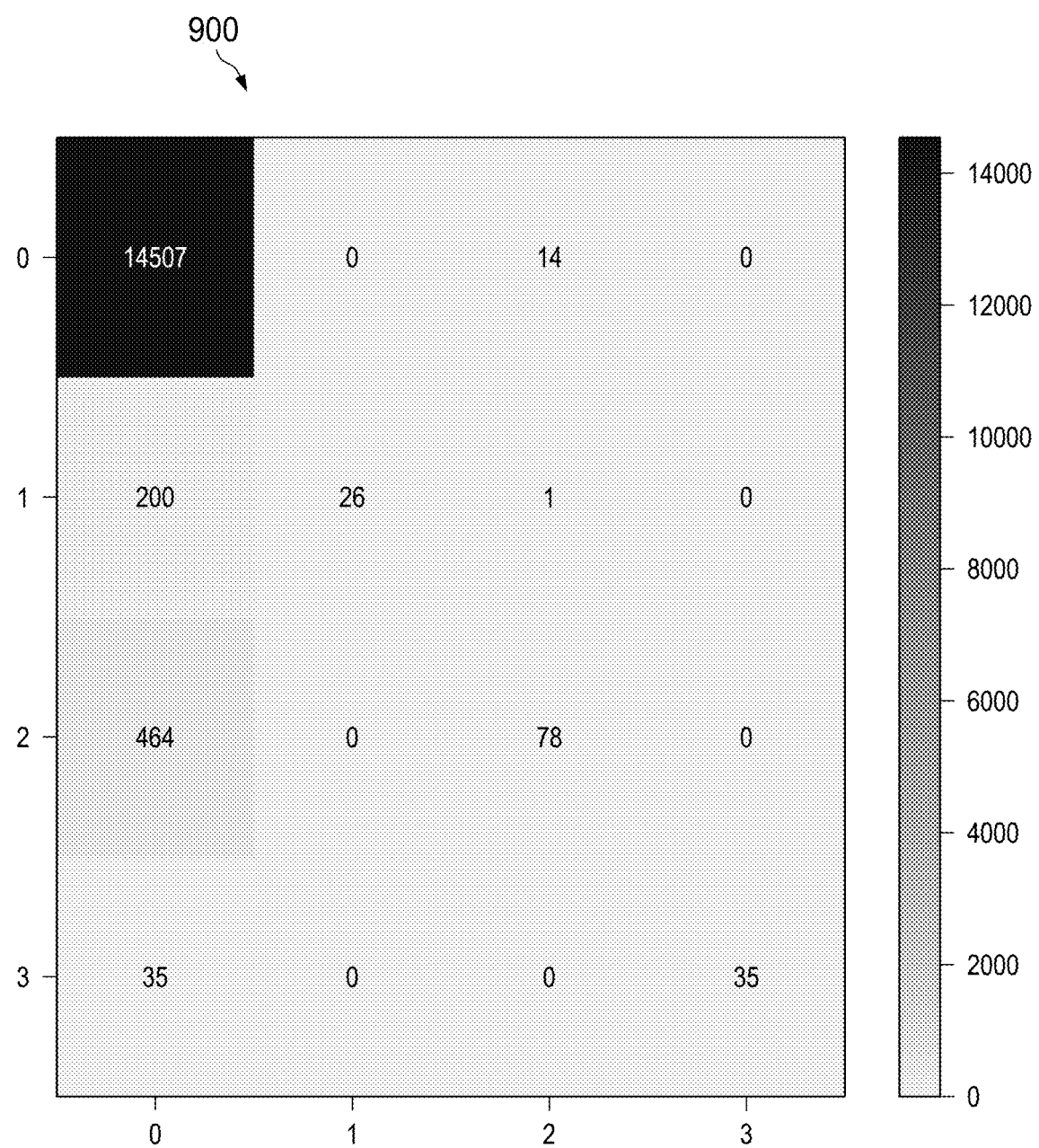
FIG. 9 is a confusion matrix of ground truth versus model prediction for a second model in the experiment.

FIG. 9 is a confusion matrix 900 of ground truth versus model prediction for a second model in the experiment. The x-axis represents model prediction. The y-axis represents ground truth. In the second model, cross-entropy was used, but the NPS pseudo color channel 420 and the entropy pseudo color channel 430 were not used. Again, diagonal elements of the confusion matrix 900 correspond to correctly-classified labelled validation images.

Using focal loss did not noticeably improve model performance in the under-represented classes, However, when comparing the confusion matrix 800 and the confusion matrix 900, it can be seen that using focal loss, the NPS pseudo color channel 420, and the entropy pseudo color channel 430 did noticeably improve performance. For instance, the number of false positives in minority classes 1, 2, and 3 decreases from 15 in the confusion matrix 800 to 4 in the confusion matrix 900.

Figure 10:
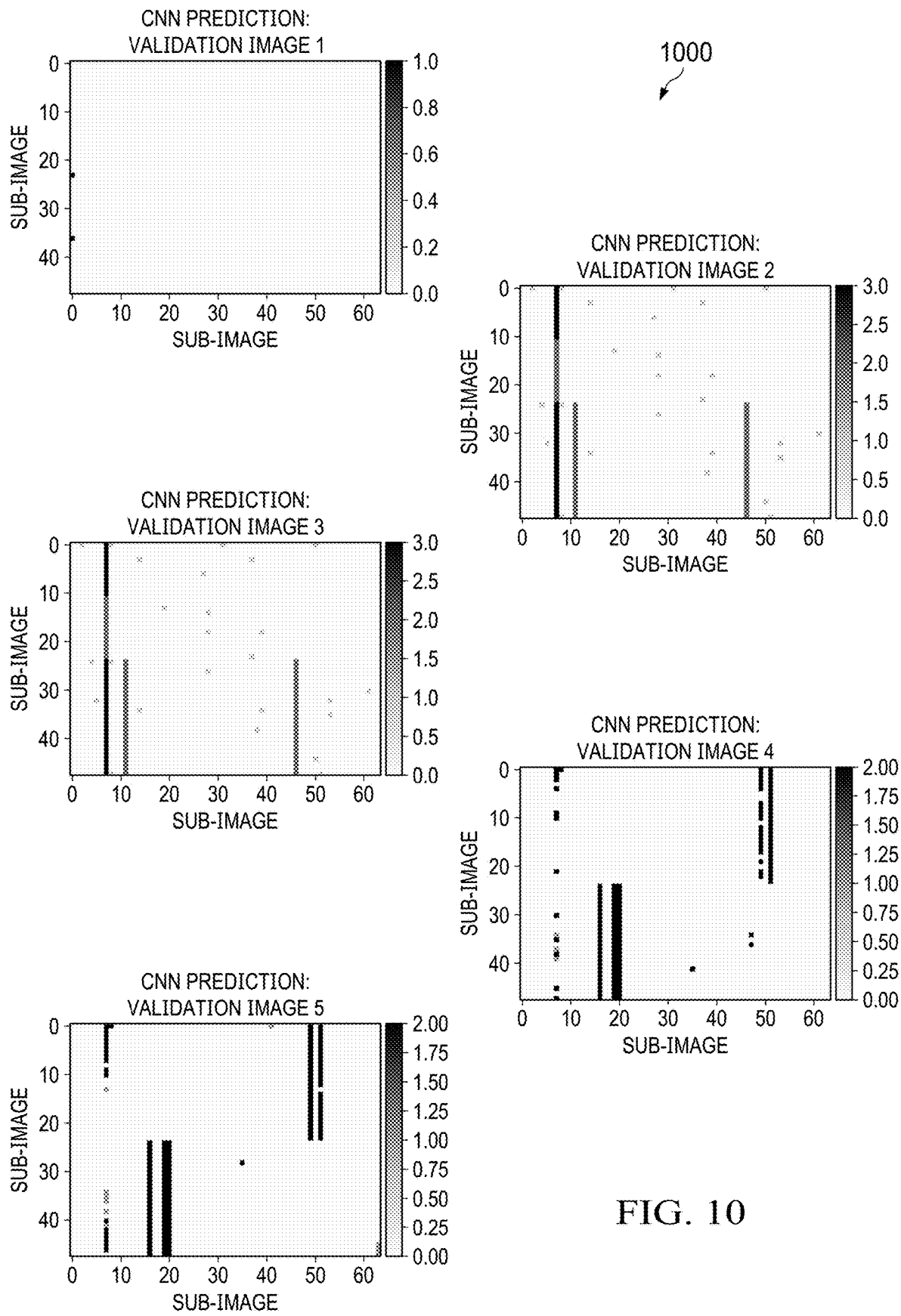
FIG. 10 shows predicted dead detector maps in the experiment.

FIG. 10 shows predicted dead detector maps 1000 in the experiment. The predicted dead detector maps 1000 were stitched together from predicted classifications for each of the labelled validation images and using the CNN with cross-entropy loss, but not using the NPS pseudo color channel 420 and the entropy pseudo color channel 430. That CNN was chosen because it had the highest average F1 score. The color scale indicates classification so that a black pixel (representing a 32×32 pixel sub-image) is predicted as having 0 dead detector elements, a white pixel (representing a 32×32 pixel sub-image) is predicted as having the maximum number of dead detector elements (either 2=1%-5% dead detectors in the sub-image, or 3=greater than 5% dead detectors in the sub-image)).

Figure 11:
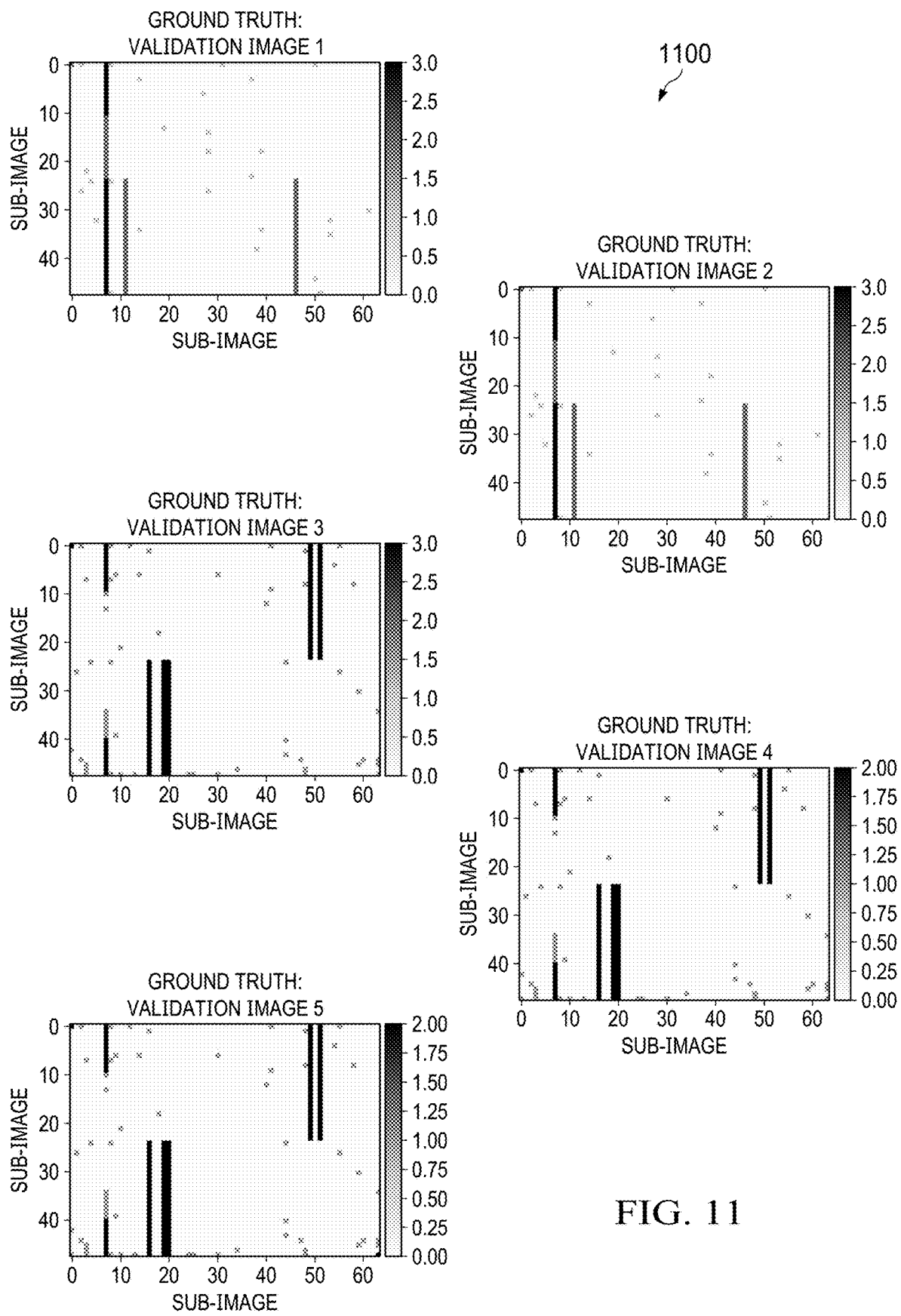
FIG. 11 shows ground truth dead detector maps presented as labelled 32×32 sub-images in the experiment.

FIG. 11 shows ground truth dead detector maps 1100 presented as labelled 32×32 sub-images in the experiment. The ground truth dead detector maps 1100 are the dead detector maps obtained in step 210 of FIG. 2. Again, the color scale indicates classification. For labelled validation image 2, the predicted dead detector map 1000 almost perfectly replicated the ground truth dead detector map 1100. For labelled validation images 1 and 3-5, the differences between the predicted dead detector maps 1000 and the ground truth dead detector maps 1100 demonstrate the conservative nature of the CNN 600 because the majority of incorrect classifications predict no dead detector element pixel.

Figure 12:
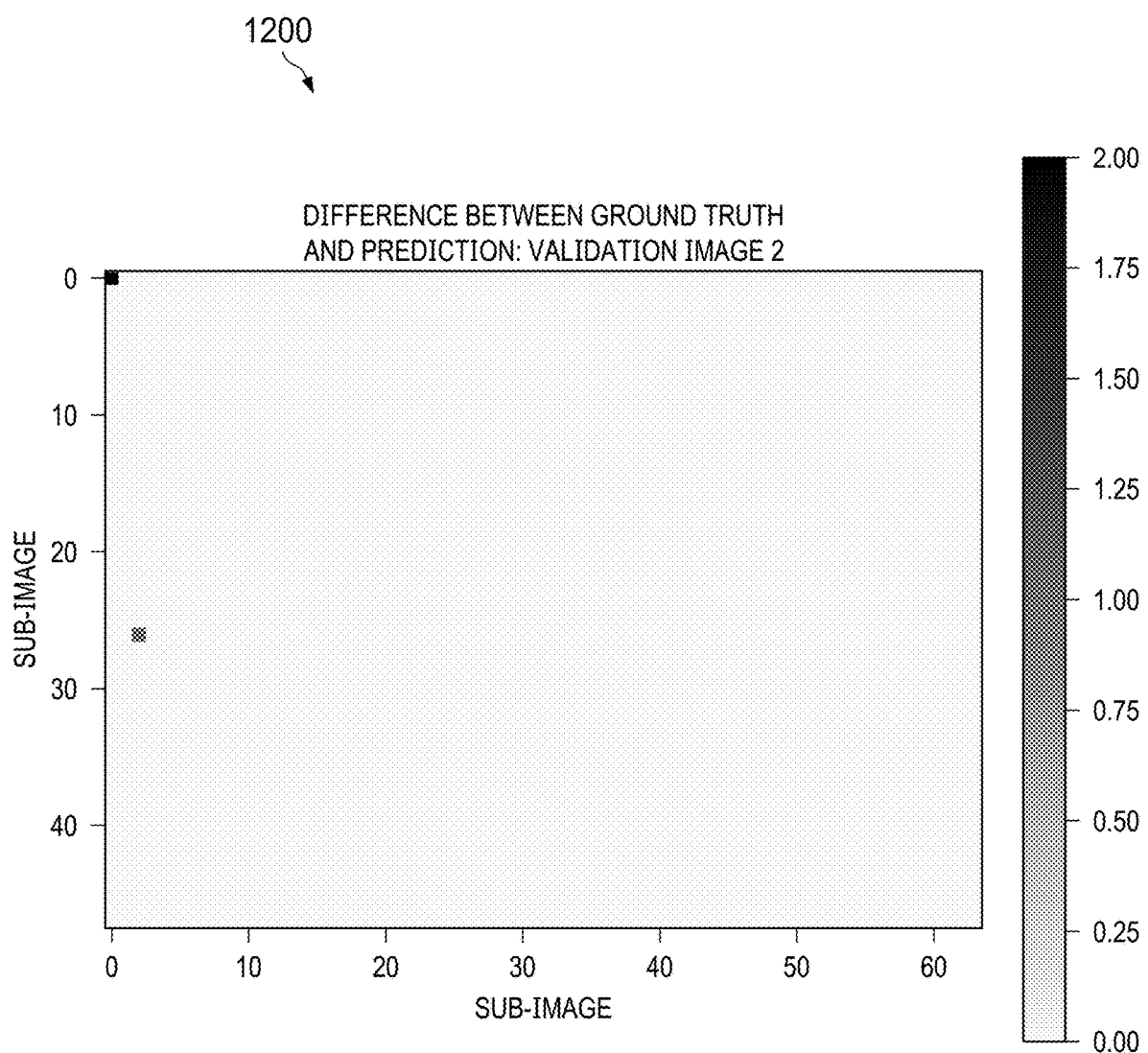
FIG. 12 shows a comparison of the predicted dead detector map in FIG. 10 and the ground truth dead detector map in FIG. 11 for labelled validation image 2.

FIG. 12 shows a comparison 1200 of the predicted dead detector map 1000 in FIG. 10 and the ground truth dead detector map 1100 in FIG. 11 for labelled validation image 2. The comparison was obtained by subtracting the ground truth dead detector map 1100 from the predicted dead detector map 1000. As can be seen, the comparison 1200 shows only two 32×32 pixel sub-images that aren't predicted perfectly.

Returning to FIG. 2, at step 280, detection of dead detector elements in a digital detector of a second DR imaging system is performed using the final machine model. For instance, flat-field images of the second DR imaging system are obtained. The final machine model is applied to those flat-field images to determine the location of every dead detector element pixel and thus dead detector element.

Finally, at step 290, it is determined whether to replace or keep the digital detector based on the detection. For instance, the digital detector is replaced if the total number of dead detector elements, the number of dead detector elements in a region of the digital detector, or the number of contiguous dead detector elements passes a threshold. The thresholds may be based on image quality, patient care, or other criteria. Alternatively, step 280 is performed at a first time and a second time, and the digital detector is replaced if the number of dead detector elements increases beyond a threshold percentage from the first time to the second time.

Figure 13:
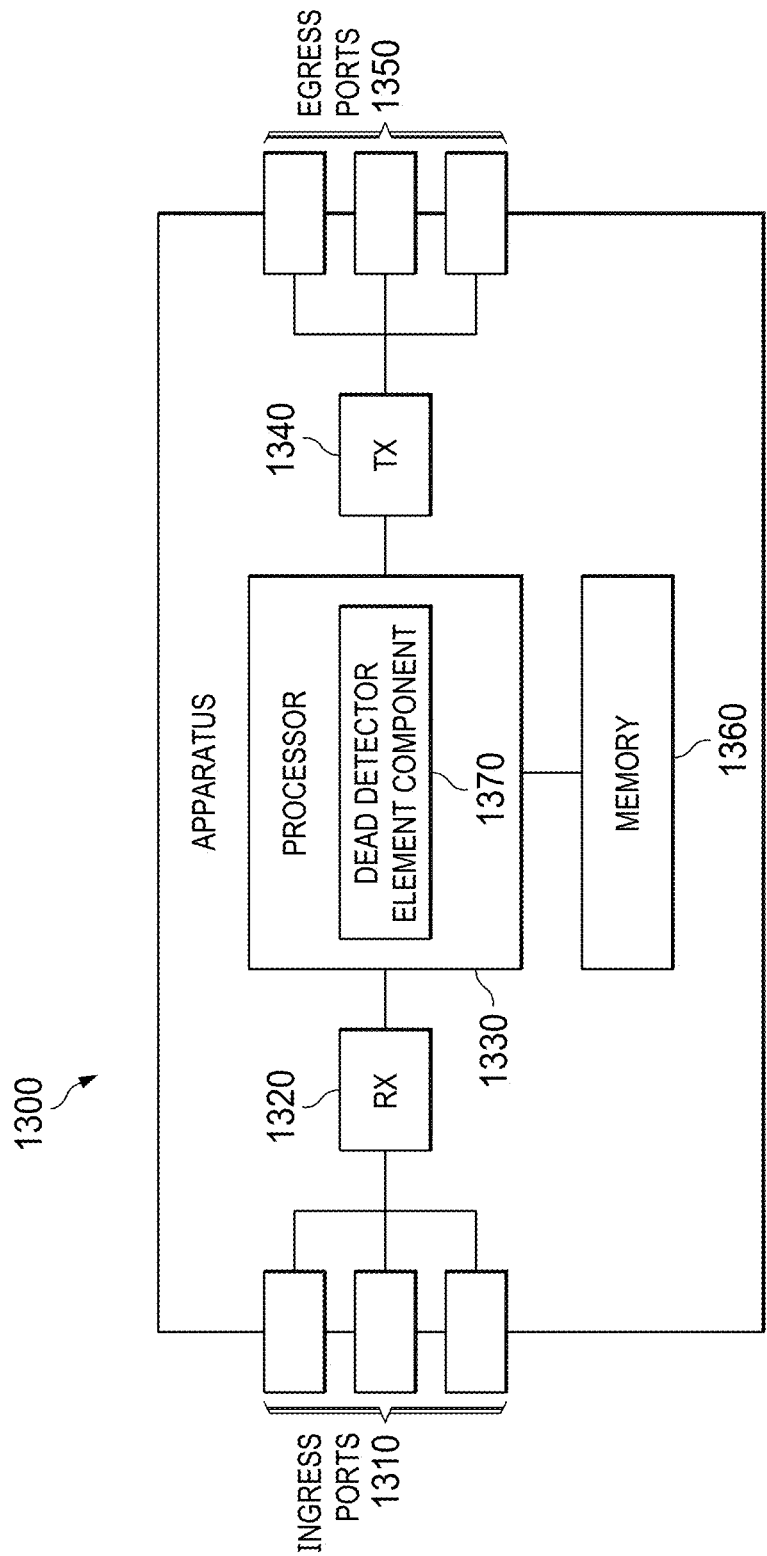
FIG. 13 is a schematic diagram of an apparatus.

FIG. 13 is a schematic diagram of an apparatus 1300. The apparatus 1300 may implement the disclosed embodiments. The apparatus 1300 comprises ingress ports 1310 and an RX 1320 to receive data; a processor 1330 or logic unit, baseband unit, or CPU, to process the data; a TX 1340 and egress ports 1350 to transmit the data; and a memory 1360 to store the data. The apparatus 1300 may also comprise OE components, EO components, or RF components coupled to the ingress ports 1310, the RX 1320, the TX 1340, and the egress ports 1350 to provide ingress or egress of optical signals, electrical signals, or RF signals.

The processor 1330 is any combination of hardware, middleware, firmware, or software. The processor 1330 comprises any combination of one or more CPU chips, cores, FPGAs, ASICs, or DSPs. The processor 1330 communicates with the ingress ports 1310, the RX 1320, the TX 1340, the egress ports 1350, and the memory 1360. The processor 1330 comprises a dead detector element component 1370, which implements the disclosed embodiments. The inclusion of the dead detector element component 1370 therefore provides a substantial improvement to the functionality of the apparatus 1300 and effects a transformation of the apparatus 1300 to a different state. Alternatively, the memory 1360 stores the dead detector element component 1370 as instructions, and the processor 1330 executes those instructions.

The memory 1360 comprises any combination of disks, tape drives, or solid-state drives. The apparatus 1300 may use the memory 1360 as an over-flow data storage device to store programs when the apparatus 1300 selects those programs for execution and to store instructions and data that the apparatus 1300 reads during execution of those programs. The memory 1360 may be volatile or non-volatile and may be any combination of ROM, RAM, TCAM, or SRAM.

A computer program product may comprise computer-executable instructions for storage on a non-transitory medium and that, when executed by a processor, cause an apparatus to perform any of the embodiments. The non-transitory medium may be the memory 1360, the processor may be the processor 1330, and the apparatus may be the apparatus 1300.

While several embodiments have been provided in the present disclosure, it may be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, components, techniques, or methods without departing from the scope of the present disclosure. Other items shown or discussed as coupled may be directly coupled or may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

What is claimed is:

1. A method comprising:
   obtaining flat-field images of a first digital radiographic (DR) imaging system;
   performing, based on the flat-field images, training and testing of an initial machine model to create a final machine model, wherein the training and testing use focal loss;
   performing detection of dead detector elements in a digital detector of a second DR imaging system using the final machine model; and
   determining whether to replace or keep the digital detector based on the detection.

2. The method of claim 1, wherein the focal loss is based on a tunable balancing parameter $\alpha_t$, a probability of an estimated class p, and a tunable focusing parameter $\gamma$.

3. The method of claim 2, wherein the focal loss uses a factor of $\alpha_t (1-p_t)^\gamma$, wherein $p_t=p$ for a most represented class of images, and wherein $p_t=1-p$ for all other classes of images.

4. The method of claim 1, further comprising processing the flat-field images to obtain processed flat-field images, wherein the processing comprises performing noise power spectrum (NPS) calculations or entropy calculations.

5. The method of claim 4, further comprising:
splitting the processed flat-field images into training images, testing images, and validation images; and
labelling the training images, the testing images, and the validation images to obtain labelled training images, labelled testing images, and labelled validation images, wherein the labelling is based on a percent of dead detector element pixels among pixels in the training images, the testing images, and the validation images.

6. The method of claim 5, further comprising performing validation of the final machine model using the labelled validation images.

7. The method of claim 1, further comprising building the initial machine model, wherein the initial machine model is a convolutional neural network (CNN) comprising convolutional layers, fully-connected layers, and a dropout layer.

8. The method of claim 1, further comprising replacing the digital detector based on the detection.

9. The method of claim 1, wherein the flat-field images are obtained without an object in a path of radiation, and wherein the flat-field images are composed of noise characteristics of the first DR imaging system and of vendor-corrected pixel data.

10. An apparatus comprising:
a memory; and
a processor coupled to the memory and configured to:
  obtain flat-field images of a first digital radiographic (DR) imaging system;
  perform, based on the flat-field images, training and testing of an initial machine model to create a final machine model, wherein the training and testing use focal loss;
  perform detection of dead detector elements in a digital detector of a second DR imaging system using the final machine model; and
  determine whether to replace or keep the digital detector based on the detection.

11. The apparatus of claim 10, wherein the focal loss is based on a tunable balancing parameter $\alpha_t$, a probability of an estimated class p, and a tunable focusing parameter $\gamma$.

12. The apparatus of claim 11, wherein the focal loss uses a factor of $\alpha_t (1-p_t)^\gamma$, wherein $p_t = p$ for a most represented class of images, and wherein $p_t = 1-p$ for all other classes of images.

13. The apparatus of claim 10, wherein the processor is further configured to process the flat-field images to obtain processed flat-field images, and wherein the processing comprises performing noise power spectrum (NPS) calculations or entropy calculations.

14. The apparatus of claim 13, wherein the processor is further configured to:
split the processed flat-field images into training images, testing images, and validation images; and
label the training images, the testing images, and the validation images to obtain labelled training images, labelled testing images, and labelled validation images, and
wherein the labelling is based on a percent of dead detector element pixels among pixels in the training images, the testing images, and the validation images.

15. The apparatus of claim 14, wherein the processor is further configured to perform validation of the final machine model using the labelled validation images.

16. The apparatus of claim 10, wherein the processor is further configured to build the initial machine model, and wherein the initial machine model is a convolutional neural network (CNN) comprising convolutional layers, fully-connected layers, and a dropout layer.

17. A computer program product comprising instructions that are stored on a non-transitory computer-readable medium and that, when executed by a processor, cause an apparatus to:
obtain flat-field images of a first digital radiographic (DR) imaging system;
perform, based on the flat-field images, training and testing of an initial machine model to create a final machine model, wherein the training and testing use focal loss;
perform detection of dead detector elements in a digital detector of a second DR imaging system using the final machine model; and
determine whether to replace or keep the digital detector based on the detection.

18. The computer program product of claim 17, wherein the focal loss is based on a tunable balancing parameter $\alpha_t$, a probability of an estimated class p, and a tunable focusing parameter $\gamma$.

19. The computer program product of claim 17, wherein when executed by the processor, the instructions further cause the apparatus to process the flat-field images to obtain processed flat-field images, and wherein the processing comprises performing noise power spectrum (NPS) calculations or entropy calculations.

20. The computer program product of claim 19, wherein when executed by the processor, the instructions further cause the apparatus to:
split the processed flat-field images into training images, testing images, and validation images; and
label the training images, the testing images, and the validation images to obtain labelled training images, labelled testing images, and labelled validation images, and
wherein the labelling is based on a percent of dead detector element pixels among pixels in the training images, the testing images, and the validation images.

21. The computer program product of claim 17, wherein when executed by the processor, the instructions further cause the apparatus to build the initial machine model, and wherein the initial machine model is a convolutional neural network (CNN) comprising convolutional layers, fully-connected layers, and a dropout layer.

* * * * *